United States Patent [19]
Nilsson et al.

[11] Patent Number: 6,137,209
[45] Date of Patent: *Oct. 24, 2000

[54] HIGH POWER ULTRASONIC TRANSDUCER

[76] Inventors: Bo Nilsson, P.O. Box 3139 K Gräsö, S-740 71 Öregrung; Håkan Dahlberg, Berghemsgatan 50, S-804 27 Gävle, both of Sweden

[ * ] Notice: This patent is subject to a terminal disclaimer.

[21] Appl. No.: 09/348,308

[22] Filed: Jul. 7, 1999

Related U.S. Application Data

[63] Continuation-in-part of application No. 09/076,112, May 12, 1998, Pat. No. 5,955,823.

[51] Int. Cl.[7] .................................................. H01L 41/08
[52] U.S. Cl. .......................................... 310/346; 310/344
[58] Field of Search ..................................... 310/344, 346

[56] References Cited

U.S. PATENT DOCUMENTS

| | | | |
|---|---|---|---|
| 4,011,474 | 3/1977 | O'Neill | 310/328 |
| 5,955,823 | 9/1999 | Nilsson et al. | 310/346 |
| 6,016,023 | 1/2000 | Nilsson et al. | 310/341 |

FOREIGN PATENT DOCUMENTS

| | | | |
|---|---|---|---|
| 1266143 | 8/1972 | United Kingdom | H04R 17/00 |

*Primary Examiner*—Thomas M. Dougherty
*Attorney, Agent, or Firm*—Young & Thompson

[57] ABSTRACT

A method to improve the high output characteristics of a ultrasonic transducer 1 by urging a cooling gas 13 to flow through the transducer, thereby passing a cooling member 18 between at least one pair of adjacent piezoelectric elements 6, 7. In a preferred embodiment sulfurhexafluoride ($SF_6$) is used as cooling gas.

7 Claims, 2 Drawing Sheets

HIGH POWER ULTRASONIC TRANSDUCER

This application is a continuation-in-part of Ser. No. 09/076,112 filed May 12, 1998, now U.S. Pat. No. 5,955,823.

TECHNICAL FIELD OF THE INVENTION

The present invention relates to ultrasonic transducers, and more specifically to high power ultrasonic transducers with piezoelectric elements for use under conditions of reduced thermal conductivity with respect to the surroundings.

PRIOR ART

Ultrasonic transducers sometimes have to be utilized under conditions of an environment having reduced thermal conductivity. For example, this is the case for submersible transducers, as well as for transducers working in surroundings of high temperatures.

Regardless of design of transducer, a high ambient temperature constitutes an environment of reduced thermal conductivity. The heat generated by the piezoelectric elements of the transducer tends to build up a high intrinsic temperature within the transducer, rather than the heat being transferred to the surroundings.

In a submersible ultrasonic transducer the heat is captured within the transducer. The casing of a submersible transducer is sealed for the transducer to be operative under water, thereby making the removal of excess heat from the transducer difficult. Numerous submersible transducers are known within the art. For example, the British patent 1 266 143 to H. J. Wollaston discloses an ultrasonic transducer wherein the oscillating piezoelectric element of a transducer is contained within a casing of tubular form.

Also conventional surface mounted transducers, for instance on the outside of a tank wall, often have to be encased and sealed to withstand harsh industrial environment, and consequently a similar situation as for submersible transducers occurs.

Thus, encasing the piezoelectric elements of a transducer will reduce the thermal conductivity between the piezoelectric element of elements and the medium surrounding the transducer, thereby reducing the cooling of the piezoelectric element(s). The temperature increase in the piezoelectric material will decrease its electromechanical efficiency and finally—typically at a temperature of about 608° F. (320° C.)—the material will depolarize and become useless.

This is especially pronounced in the case of high power transducers, wherein the higher power applied can generate considerable internal heat in the piezoelectric elements as well as in the encasement of the transducer, especially if the total resonance system does not have a proper acoustical and electrical tuning.

In addition, the lifetime of a high power ultrasonic transducer is also reduced by phenomena such as corona discharge and arc over, between edges of adjacent piezoelectric disk elements being stacked upon each other with conductive layers, e.g. plates or disks, as electrical poles sandwiched between the disk elements. If any organic material is present corona discharges will produce conductive carbon layers, and when the distance between different electrical polarities diminish, an arc over will appear. Arcs deteriorate the piezoelectric material. Although these phenomena are not limited to encased transducers only, the occurrence of arcs is still a disadvantage in addition to the degeneration caused by high temperature.

The conventional way to reduce the arc effect has been to immerse the stack of piezoelectric elements in an insulating medium, but this has also the effect to further reduce the thermal conductivity between the piezoelectric elements and the surrounding of the transducer.

In U.S. Pat. No. 4,011,474, C. G. O'Neill discloses a transducer with improved characteristics in this respect, the improvement begin that a dielectric medium is applied with pressure to the radial ends of disk shaped piezoelectric elements. The dielectric medium may be a solid material or a fluid, preferably a liquid.

Although a dielectric medium applied with pressure to the piezoelectric degrading arcs, the problem of low thermal conductivity remains.

SUMMARY OF THE INVENTION

It is an object of the present invention to provide an ultrasonic transducer for generating high power ultrasonic vibrations with improved efficiency.

This object is achieved by a method according to claim 1 of the appended claims, wherein is defined a method for cooling the piezoelectric elements of the transducer by the flow of a coolant.

In a preferred embodiment of the invention, the coolant is a gas with the ability to suppress to the corona and arc phenomena. In a most preferred embodiment the gas has sulfurhexafluoride $SF_6$ as a main component.

In a second aspect of the invention is provided an ultrasonic transducer device according to claim 5, wherein is defined a design for an ultrasonic transducer device for use with the method of the invention.

BRIEF DESCRIPTION OF THE DRAWINGS

An ultrasonic transducer device for use with the method according to the invention will be described, by way of an example only, with reference to the attached drawings, wherein.

DETAILED DESCRIPTION OF EMBODIMENTS

The temperature of piezoelectric elements in an ultrasonic transducer will increase during operation because of the friction within the piezoelectric materials and also because acoustic energy is trapped inside the transducer if the transducer system is not properly tuned. Therefore, it becomes obvious that the piezoelectric material can only transmit ultrasonic energy at a level that allows the material to work at a temperature so low, that it can maintain its effective properties during its useful lifetime.

According to the present invention, a method that allows an encased ultrasonic transducer with stacked piezoelectric elements to transmit ultrasonic energy at a raised level by way of cooling the piezoelectric elements includes the steps of:

providing the transducer with at least one gas inlet and at least one gas outlet;

providing a gas conducting means for cooling the piezoelectric elements between at least one pair of adjacent elements, such that a gas from the gas inlet can flow through the gas conducting means to be discharged out through the gas outlet of the transducer;

selecting a cooling gas; and by utilizing an external pressure source urge said cooling gas to flow through the gas connecting means thereby cooling the adjacent piezoelectric elements.

A preferred embodiment of an ultrasonic transducer to be used with the method of the invention shall now be described with reference to FIG. 1.

Figure 1:
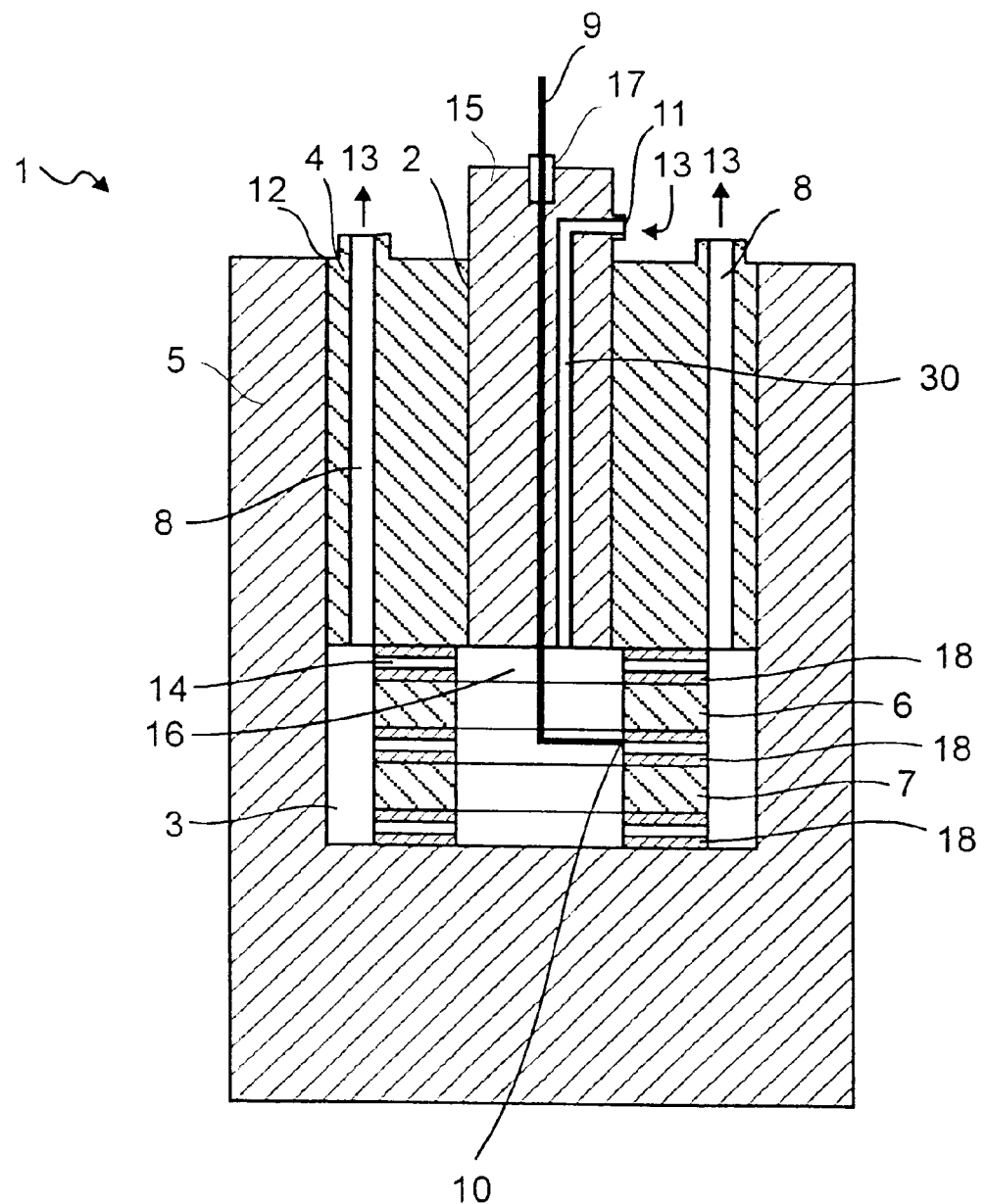
FIG. 1 is a cross-sectional elevation view of an embodiment of a transducer according to the invention.

According to FIG. 1, the illustrated embodiment of a transducer 1 according to the invention includes a cylindrical metal housing acting as a resonance body, consisting of an upper 4 and lower 5 cylindrical housing body fixed to each other e.g. by welding 12, a central cylindrical channel 2 in the upper housing body and a hollow cylindrical chamber 3 defined by the upper and lower housing bodies. In the chamber there are two ring shaped piezoelectric elements 6, 7 disposed in such a way that a central axis of each of the elements 6, 7 substantially coincides with a central axis of the housing 1 running in the center of the channel 2.

Between the upper housing body 4 and the upper piezoelectric element 6 there is a metal cooling member 18 disposed with direct physical contact between each adjacent parts, thereby also providing electrical connection between them. A second metal cooling member 18 is disposed between the piezoelectric elements 6, 7 and further a third metal cooling member 18 is disposed between the lower piezoelectric element 7 and the lower housing body 5. In order to reach proper physical and/or electrical contact it is optional to insert conductive shims between adjacent parts, but since this is not mandatory these are not shown in the present embodiment.

Channels 8 that connect the chamber 3, and more specifically that part of the chamber that is surrounding the piezoelectric elements 6, 7 as well as the cooling members 18, are provided in the upper housing body 4 for gas communication with the outside of the transducer.

The material of the piezoelectric elements 6, 7 may be any suitable ceramic material as is well known within the art, such as leadzirconate titanate (PZT), lead titanate (PT), lead metaniobate and bismut titanate. The metal of the housing bodies 4, 5 is preferably stainless steel. In the present embodiment each cooling member 18 is a steel disk with a central hole 16 and at least one, preferably several radial holes 14 allowing gas to flow through the holes at the same time as the cooling members provide electrical and thermal conduction through the surfaces where they abut the piezoelectric elements 6, 7 and the upper and lower housing bodies 4, 5.

As is well known within the art, the piezoelectric elements 6, 7 have to be pre-stressed in order to work efficiently. The pre-stressing operation has to be done before the upper and lower housing bodies 4, 5 are fixed to each other, and can be performed by any suitable technique well known within the art.

The central cooling member 18 is electrically connected, for example by a welded joint 10, to a metal rod 9. The rod is inserted through the central passage of a hollow sleeve 15, e.g. made of polytetrafluoroethylene, fitted into the channel 2. The rod extends through a sealed hole 17 in the end of the sleeve, to be connected to an external control and power unit (not shown). A ground potential is provided to the metal housing 4, 5.

A channel 30 is provided through the sleeve 15. The channel connects a gas inlet orifice 11 in the sleeve to the chamber 3, and more specifically to the part of the chamber that is defined by the central holes of the cooling members 18 and piezoelectric elements 6, 7, respectively. A suitable tubing can be attached to the gas inlet orifice in order to connect to a suitable, conventional gas and pressure source (not shown). Although only one channel 30 is shown in FIG. 1, more than one such channel could be provided in order to achieve an even flow distribution within the chamber 3.

Thus, a cooling gas 13 can be introduced through the gas inlet orifice 11 into the channel 30 by applying a proper pressure, preferably within the range of 3 psi to 30 psi. The gas will flush in the central holes of the cooling members 18 and through the radial holes 14, thereby receiving heat from the piezoelectric elements 6, 7 via the cooling members and finally being discharged through the outlet channels 8. Thus, internal heat in the piezoelectric elements is transported from the inside of the transducer to the outside in a controlled way.

Preferably, the outlet channels 8 are connected by tubing to a heat exchange device to cool the gas to enable it to be circulated through the transducer in a closed circulation system. However, since this arrangement is optional, could be realized with any suitable conventional equipment known by those skilled in the art, and further is outside of the novel aspect of the invention, such a closed circulating system is not illustrated in FIG. 1.

In operation, the control and power unit provides an alternating voltage of a level and frequency selected to suit the application at hand, such as a peak-to-peak voltage of 10 000 volts at a frequency of 25 kHz, to the piezoelectric elements 6, 7, thus bringing them to vibrate in a manner well known within the art.

At the same time, the gas 13 is forced by the gas and pressure source to flow between the piezoelectric elements 6, 7, as described above, to cool the elements and thereby keep them at a low and efficient working temperature.

Figure 2A:
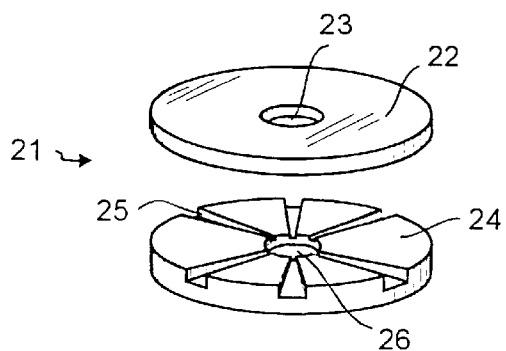
FIG. 2A is an exploded view of two parts of an embodiment of a cooling member of the invention.
Figure 2B:
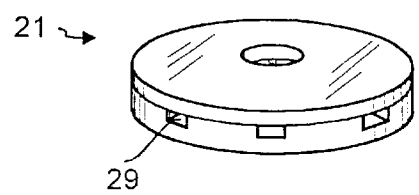
FIG. 2B is a perspective view of the parts shown in FIG. 2A when assembled to the cooling member.

A preferred embodiment of a cooling member for use with the invention is configured as a cooling disk assembly 21, as shown in FIG. 2A and 2B, wherein in FIG. 2A the parts of the assembly are shown separated while they are shown assembled in FIG. 2B.

It should be noted that in order to make the illustrations more easy to read, the dimensional proportions of the parts forming the cooling disk assembly 21 shown in FIG. 2A and 2B deviates from those of the corresponding cooling members 18 shown in FIG. 1.

The upper disk element 22 is provided with a central hole 23 and has plane upper and lower surfaces. The lower disk element 24 has a central hole 26 of the same size as the central hole 23 and a plane bottom surface (not shown), and is on its upper surface provided with grooves 25. The grooves are equally spaced apart and radiate from the hole 26 out the peripheral edge of the disk element.

As shown in FIG. 2B, when the disk elements 22, 24 are assembled to form a cooling member 21 the grooves 25 are covered by the upper disk element 22, thereby forming channels 29 through which a cooling gas can flow.

This embodiment of a cooling member has the advantage of providing large and flat contact areas between the cooling member and the piezoelectric elements thereby providing an optimal heat transfer and minimized mechanical contact pressure, at the same time as it allows for low manufacturing costs.

Figure 3:
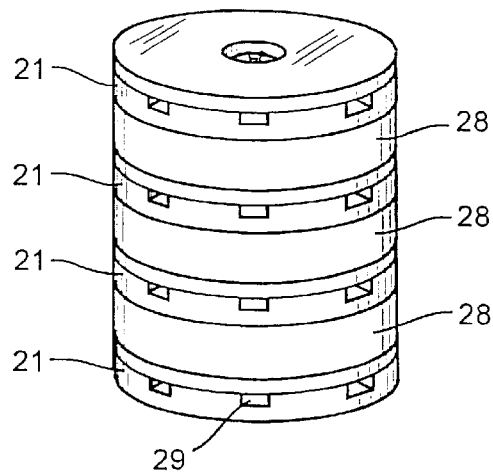
FIG. 3 is a perspective view of a stack of piezoelectric elements and cooling members according to FIG. 2B, for use in an embodiment of a transducer according to the invention.

FIG. 3 shows a stack of alternating piezoelectric elements 28 and cooling members 21 for use in an embodiment of a transducer with more than two (in this case four) piezoelectric elements. In addition to placing cooling members between the piezoelectric elements, cooling members are also provided between the outermost piezoelectric elements of the stack and their respective adjacent housing body surfaces (similar to the double piezoelectric element stack in FIG. 1). Each cooling member is of the embodiment shown in FIG. 2B. As can be seen, each cooling member is placed such that its radial channels 29 are placed straight over the radial channels of the other cooling members, when viewed from above. Although any arrangement of the channel is possible and effective, this arrangement is assessed to be advantageous in that it offers the best possible acoustical characteristics.

An ultrasonic transducer according to the invention is able to convert a higher ratio of the applied voltage to ultrasonic energy compared to conventional transducers due to the system for cooling the piezoelectric elements within the transducer. This cooling also enables the piezoelectric elements to withstand higher applied voltage than would be possible without the cooling, thus raising the efficiency and the lifetime of the transducer. It is also possible to use a transducer according to the present invention in higher ambient temperatures than is possible with a conventional transducer.

As described above, it is preferable to provide a cooling member between each pair of adjacent piezoelectric elements as well as on each end of the piezoelectric element stack in order to obtain maximum cooling efficiency. However, it is of course possible to replace some of these cooling elements with an element lacking cooling channels if this should be preferred, while still achieving a cooling effect, but this reduces the cooling efficiency, and it is also likely that it reduces the longevity of the adjacent piezoelectric element(s).

As is also described above, it is preferred that the cooling gas flow is supplied into the central hole of the stack of piezoelectric elements and cooling members. This flow direction is preferred since it is presumed that it represents a favorable and efficient flow path. The flow direction could, however, be the opposite as well.

It should be noted that the dimensions of the components, as well as of the assembled transducer, have to be selected to suit the application at hand. Thus, the transducer should be dimensioned according to common principles valid for transducer systems, and preferably tuned to work at acoustical and electrical resonance in order to give highest possible output efficiency.

Numerous gases could be utilized for the purpose of cooling the piezoelectric elements, though a general requirement is that the gas has to be sufficiently inert not to damage any parts of the transducer. Further, it should have good thermal conductivity properties.

Therefore, suitable gases include nitrogen, hydrogen, carbon dioxide, Freon 12 and ammonia.

However, the most preferred gas to be used with the cooling system of the invention is sulfurhexafluoride, $SF_6$.

$SF_6$ has excellent thermal capacity $c_p$ which, for example, is in the order of two to three times higher than any of the other gases mentioned above.

Further, $SF_6$ is also an excellent dielectricum. This property of $SF_6$ could be advantageously utilized in a transducer according to the invention, since it has a reducing effect on the arc phenomena occurring at high electromagnetic field intensities as present near the edges of the piezoelectric elements.

It should be pointed out that since the present invention makes it possible to utilize higher electrical voltages than for a similar conventional transducer, the distances between parts of different electrical potential should normally be extended, as compared to conventional transducers, to avoid arc over. The use of $SF_6$ gas reduces, or may even eliminate, this need for increased distances. However, for safety reasons there should be installed an automatic electricity cut off system to, if the gas pressure becomes too low in the circulation system, avoid short circuits or other electric hazards.

Tests performed by the inventor, wherein the voltage applied to the transducer where monitored on an oscilloscope, showed that interfering peaks on the voltage curve appearing when operating the transducer with air or $CO_2$, and attributable to the occurrence of coronas, where in practice completely eliminated when instead $SF_6$ was circulated through the transducer.

Further, the tests revealed that ultrasonic transducers according to the invention, using $SF_6$ as a coolant, showed similar long term properties when provided with a voltage of 12 000 V and 20 kHz as a typical conventional transducer provided with a voltage of 900 V and 22 kHz.

Although $SF_6$ is the most preferred gas to be used with the present invention, it should be noted that $SF_6$ also has some less pleasant characteristics which have to be considered when designing a transducer for the application at hand.

Thus, it is known that under the influence of very strong electric fields, typically more than 100 000 volts, $SF_6$ can interact with a variety of compounds, including moisture, to produce gases and ions that finally degrade and destroy a high voltage device. It is therefore essential that high voltage devices contain little or no degradable compounds such as phenolic resins, glass, glass reinforced materials or porcelain near the high voltage fields in the $SF_6$ atmosphere. Since a high voltage piezoelectric transducer normally operates at voltages below 20 000 V, it is clear that $SF_6$ can be used to suppress corona discharge and the like in such a transducer.

Also, $SF_6$ is an environmental hazard. Specifically, it has been classed as a potent greenhouse gas by scientists on the Intergovernmental Pancl on Climate Change. Therefore, care must be taken that it does not escape to the atmosphere.

A $SF_6$ cooling system for ultrasound transducers should therefore preferably be conceived and realized as a closed system in which $SF_6$, being warmed up in the ultrasound transducers is cooled outside of the transducers before it is pumped through the ultrasound transducers again.

While the invention has been described in detail with respect to specific preferred embodiments thereof, it will be appreciated upon a reading and understanding of the foregoing that numerous variations may be made to those embodiments which nonetheless lie within the scope of the appended claim.

What is claimed is:

1. A method for improving the output of an ultrasonic transducer, the transducer being of the type employing at least two piezoelectric elements wherein the piezoelectric elements are stacked serially and an alternating voltage is applied to the opposing surfaces of the elements for that purpose of causing them to change their dimensions in response thereto, and the transducer further being of the type with the piezoelectric elements encased in a fluidum-tight casing and still further the transducer through its casing is provided with at least one inlet conduit for supplying a gas and at least one outlet conduit for discharging the gas, the method comprising the steps of:

providing a gas conducting means between at least one pair of adjacent piezoelectric elements for cooling the piezoelectric elements, said gas conducting means provided with at least one channel providing a gas flow path through the gas conducting means, and said conducting means being so arranged that the inlet conduit is in flow communication with the inlet of said channel and the outlet of said channel is in flow communications with the outlet conduit;

selecting and providing a cooling gas;

forcing said cooling gas into the inlet conduit, thereby urging it to flow through said gas conducting means for cooling of the adjacent piezoelectric elements whereby the temperature of said cooling gas is raised, and discharging said cooling gas of elevated temperature through the outlet conduit.

2. The method according to claim 1, wherein said step of selecting a cooling gas includes the step of selecting said gas from the group of gases consisting of: nitrogen, hydrogen, carbon dioxide, Freon 12, ammonia and sulfurhexafluoride $SF_6$.

3. The method according to claim 1, wherein said step of selecting a cooling gas further comprises the step of selecting said cooling gas according to its dielectrical properties in order to suppress arc over within the transducer.

4. The method according to claim 3, wherein said step of selecting a cooling gas of suitable dielectrical properties comprises the step of selecting sulfurhexafluoride ($SF_6$) as said cooling gas.

5. An ultrasonic transducer device employing at least two piezoelectric elements, wherein the piezoelectric elements are stacked serially and are provided with means for electrically connecting them to an alternating voltage source applied to the opposing surfaces of the elements for the purpose of causing them to change their dimensions in response thereto, and the piezoelectric elements are encased in a gas-tight casing, and at least one inlet conduit for supplying a gas and at least one outlet conduit for discharging the gas are provided through the casing, the ultrasonic transducer device comprising:

a gas conducting means disposed between at least one pair of adjacent piezoelectric elements for cooling the piezoelectric elements with a cooling gas, wherein said gas conducting means has least one central hole in flow communication with the outlet conduit, and an outer rim surface in flow communication with the outlet conduit, said gas conducting means further provided with at least one channel providing a gas flow path through the gas conducting means, between the inlet conduit and the outlet conduit.

6. The ultrasonic transducer device according to claim 5, wherein said gas conducting means is a metal disk element.

7. The ultrasonic transducer device according to claim 6, wherein said metal disk element is an assembly of a first disk shaped plate with a first central hole and a second disk shaped plate with a second central hole, said second disk shaped plate on one flat surface provided with at least one groove connecting the radial inner rim of the disk with its radial outer rim, and the plates are assembled such that the first plate covers the at least one groove to define a passage through the assembly.

* * * * *